United States Patent [19]

Berger et al.

[11] Patent Number: 5,102,222
[45] Date of Patent: Apr. 7, 1992

[54] LIGHT WAVE POLARIZATION DETERMINATION USING A HYBRID SYSTEM

[75] Inventors: Josef Berger; Yishai Kagan; Doron Mick, all of Santa Clara; Moshe Nazarathy, Palo Alto, all of Calif.

[73] Assignee: Harmonic Lightwaves, Inc., Santa Clara, Calif.

[21] Appl. No.: 477,305

[22] Filed: Feb. 8, 1990

[51] Int. Cl.⁵ .............................................. G01J 4/04
[52] U.S. Cl. ................................... 356/367; 356/365
[58] Field of Search ............... 356/364, 365, 366, 367, 356/369; 350/400, 401

[56] References Cited

U.S. PATENT DOCUMENTS

| | | | |
|---|---|---|---|
| 3,430,048 | 2/1969 | Rubinstein | 356/401 |
| 3,556,662 | 7/1971 | Levenstein et al. | 356/365 |
| 3,985,447 | 10/1976 | Aspres | 356/369 |
| 4,158,506 | 6/1979 | Collett | 356/365 |
| 4,482,250 | 11/1984 | Hirvonen et al. | 356/369 |
| 4,492,436 | 1/1985 | Bergmann | 350/395 |
| 4,539,521 | 9/1985 | Matsumoto | 356/364 |
| 4,584,470 | 4/1986 | Iizuka et al. | 356/365 |
| 4,585,348 | 4/1986 | Chastang et al. | 356/369 |
| 4,653,867 | 3/1987 | Urabe et al. | 350/351 |
| 4,685,773 | 8/1987 | Carlsen et al. | 350/401 |
| 4,702,557 | 10/1987 | Beckmann et al. | 350/330 |
| 4,720,162 | 1/1988 | Mochizuki et al. | 350/96.15 |
| 4,761,050 | 8/1988 | Byron | 350/96.15 |

FOREIGN PATENT DOCUMENTS 3228910  2/1984  Fed. Rep. of Germany ..... 356/73.1

OTHER PUBLICATIONS

Vergnes et al., "Ellipsometry Without a Compensator-Two Improvements in Speed and Reliability of the Monin and Boutry Method", *Optics Communications*, vol. 32, No. 1, (Jan. 1980), pp. 5-10.

Okoshi et al., "Polarization-Diversity Receiver for Heterodyne/Coherent Optical Fiber Communications", The Fourth IOOC Paper, No. 30C3-2, Jun. 27-30, 1983, Tokyo, Japan.

Jellison, "Four-Channel Polarimeter for Time-Resolved Ellipsometry", *Optics Letters*, vol. 12 (1987), pp. 766-768.

Kasovsky, "Phase- and Polarization-Diversity Coherent Optical Techniques", I.E.E.E. Jour. of Lightwave Technology, vol. 7 (1989), pp. 279-322.

*Primary Examiner*—Richard A. Rosenberger
*Attorney, Agent, or Firm*—Schneck & McHugh

[57] ABSTRACT

Apparatus and method for determining dynamically the polarization vector direction, or polarization vector components and associated temporal phase angle, of a light beam. The apparatus includes a compact polarization beam splitter that receives a beam of light, separates the beam into two perpendicular polarization components and directs these components to a pair of optical detectors and associated circuits that form the sum and difference signals of the electrical signals produced by the optical detectors. This produces a projection of the polarization vector on a given direction. If the light is generally elliptically polarized, use of two such polarization beam splitters and four optical detectors allows reconstruction of the polarization ellipse for the light beam. Alternatively, use of one such polarization beam splitter, two optical detectors and a rotating wave plate in a multiplexed configuration allows reconstruction of the polarization ellipse. The polarization detector is very compact and may be housed in a container that is no more than a few cm. in diameter.

15 Claims, 5 Drawing Sheets

LIGHT WAVE POLARIZATION DETERMINATION USING A HYBRID SYSTEM

TECHNICAL FIELD

This invention relates to determination of the polarization state of a light wave.

BACKGROUND OF THE INVENTION

Many processing techniques for light waves require that the polarization state of the light wave be determined quickly and accurately. As used herein, the word "light" refers to an electromagnetic signal of any frequency. Because the polarization state of an incident light wave can vary with time, determination of the polarization state as time proceeds is a challenge, especially if the determination is to be made with only a small time delay.

In certain heterodyne and homodyne coherent optical communication schemes, the electrical field of the received light wave must be aligned with the optical field of a local oscillator to give maximum photodetector current. Fluctuation of polarization direction or state induced on the incident light wave during its propagation results in an unacceptable increase in the bit error rate for the message transmitted. In order to overcome the signal fading problems, certain polarization diversity apparatus has been proposed and demonstrated by various workers in the field. In these schemes, the light wave received is separated into two orthogonally polarized components and each component is heterodyned and detected separately. The two components are then amplified and summed to produce a polarization signal for further processing. In some of these apparatus, the relative phase shift between the two components is determined or corrected and the polarization angle is adjusted for maximum signal-to-noise ratio. Moreover, this is usually done over relatively long time intervals and requires relatively complex apparatus for this purpose.

In another field of application, electrical current measurements are made using fiberoptic sensors based on the Faraday rotation effect. When electric current flows in the vicinity of an optical fiber, the induced magnetic field in the fiber changes the state of polarization of a light beam propagating in the fiber. Analysis of this polarization rotation allows a determination of the magnitude of electrical current. These applications, and others as well, may use different types of polarization diversity receivers ("PDRs") that have been assembled using a variety of polarization beam splitter elements. These elements include polarizer beam splitter cubes, Glan-Thompson beam splitter polarizers and Wollaston prism polarizers. A beam splitter cube has the advantage of low cost and 90° separation of the polarization components. However, the cube provides a relatively poor extinction ratio (about 100:1). The Wollaston prism and Glan-Thompson polarizing beam splitter have high extinction ratios (about $10^5$:1) but have a small angular separation and are very costly due to incorporation of expensive optical elements therein.

In a PDR, the incident light wave is usually coupled through a lens or other optical focusing element to the polarizing beam splitter and is separated into two orthogonal polarization components, with each component falling on a separate optical detector. If the incident light wave is coupled into the PDR through a single mode fiber for application in high speed data communications and for fiber optic sensors, the alignment tolerances become very stringent, and optical components of relatively large size are no longer suitable.

Okoshi et al., in "Polarization-Diversity Receiver for the Heterodyne/Coherent Optical Fiber-Communications," The Fourth IOOC Paper, No. 30C3-2, June 27-30, 1983, Tokyo, Japan, discuss the use of a PDR together with two linearly polarized local oscillator beams to determine the relationship of two orthogonal polarization components of an incident light beam. This requires additional components such as half wave plates and requires that the ratio of power contained in two portions split from the light beam be controlled.

Jellison, in "Four-channel polarimeter for time-resolved ellipsometry," Optics Letters, vol. 12 (1987), pp. 766-768, describes recent measurements and apparatus made by many works in the field of polarization determination. These devices rely upon ellipsometry, two-channel polarimetry, four-channel polarimetry, phase retardation and other techniques to determine one or more of the parameters needed to specify the polarization state of a light beam. Kasovsky, in "Phase- and Polarization-Diversity Coherent Optical Techniques," Jour. of Lightwave Technology, vol. 7 (1989), pp. 279-322, reviews the advantages and disadvantages of several optical parameter diversity techniques.

Polarization beam splitters have been used for optical beam splitting and combining by previous workers. Use of a birefringent material as a polarization-dependent beam splitter is disclosed by Bergmann in U.S. Pat. No. 4,492,436. An optical beam with TE or TM polarization approaches the crystal at a large incidence angle. A beam with one of these two polarizations is reflected at the crystal, and a beam with the other of these two polarizations is transmitted by the crystal.

A polarization-dependent beam.splitter, possibly two right angle prisms joined at the hypotenuse, disclosed in U.S. Pat. No. 4,653,867 issued to Urabe et al., is used to combine two optical beams with perpendicular polarizations with a resulting small angular offset.

Carlson et al., in U.S. Pat. No. 4,685,773, disclose a birefringent optical multiplexer/demultiplexer with flattened bandpass that uses a first polarization beam splitter to separate an optical beam into two component beams with perpendicular linear polarization vectors. The two component beams then propagate in parallel through a plurality of birefringent crystals, in order to alter the two polarization vectors relative to one another, and are recombined using a second polarization beam splitter.

U.S. Pat. No. 4,702,557, issued to Beckmann et al., discloses an optical branching device that uses a prism and a rhombohedral plate, both optically transparent and each having a planar face, with the two planar faces being parallel and facing one another. A thin film of birefringent liquid crystal is positioned between and contiguous to these two planar faces, with a refractive index n that matches the refractive index of only one of the prism material ($n_1$) and the plate material ($n_2$). The angle of incidence $\Theta$ of the optical beam on the liquid crystal film is selected so that $\sin \Theta > n_i/n$ ($n_i < n$; i = 1 or 2). One of two perpendicular linear polarization components of an optical is completely reflected, and the other polarization component is transmitted with little or no reflection losses. This device separates an optical beam into two component beams with perpendicular linear polarization vectors.

Mochizuki et al., in U.S. Pat. No. 4,720,162, disclose use of a polarization beam splitter to receive light beams from two light sources and to issue a single output light beam propagating in a predetermined direction. The two input light beams arrive at the beam splitter from perpendicular directions, only one of the two light sources is operative at a given time, and the two incoming light beams are assumed to each be linearly polarized with perpendicular polarization vectors.

An optical switching device employing a polarization-maintaining input optical coupler and a birefringent crystal is disclosed by Byron in U.S. Pat. No. 4,761,050. The birefringent crystal acts as a polarization beam splitter to provide two optical propagation paths therein, one path for each of two component beams having perpendicular linear polarization vectors. Only one of the two polarization component beams issues from the system, depending upon whether the optical coupler receives, or does not receive, an externally controlled, switchable pump signal.

What is needed here is apparatus for determination of the instantaneous polarization state of an incident light wave that is accurate and fast enough to follow the variation in polarization state of the light wave. Preferably, the operational part of the apparatus should be relatively small in size (linear dimension less than a few cm) and be contained in a single chip, and the apparatus should be relatively simple, with few or no moving parts that can become misaligned. The hybrid should be contained on a single substrate and should include, if desired, the electronics for signal processing.

SUMMARY OF THE INVENTION

These needs are met by apparatus that incorporates in a single integrated circuit chip a polarization beam splitter of small dimension that receives a light beam and produces two orthogonal, linearly polarized light beams therefrom. A beam director receives the light beam and directs it toward the beam splitter. First and second transducers are positioned to receive the first and second polarization components of the light beam and to produce first and second electrical signals therefrom. Circuitry, positioned in the chip or elsewhere, can amplify and form the sum, difference product and other useful functions of these signals to allow a determination of the instantaneous polarization state of the incident light wave as a function of time.

In a second embodiment, a second polarization beam splitter is added to produce third and fourth orthogonal polarization components of the portion of the incident light beam. Third and fourth transducers are added to produce third and fourth electrical signals from the third and fourth polarization components of the light beam. The four electrical signals are then used to reconstruct the polarization state of a general, elliptically polarized light beam whose state may vary with time. These four electrical signals may also be provided using a single polarization beam splitter, a rotating wave plate, and a signal storage or time delay device.

BEST MODE FOR CARRYING OUT THE INVENTION

Figure 1:
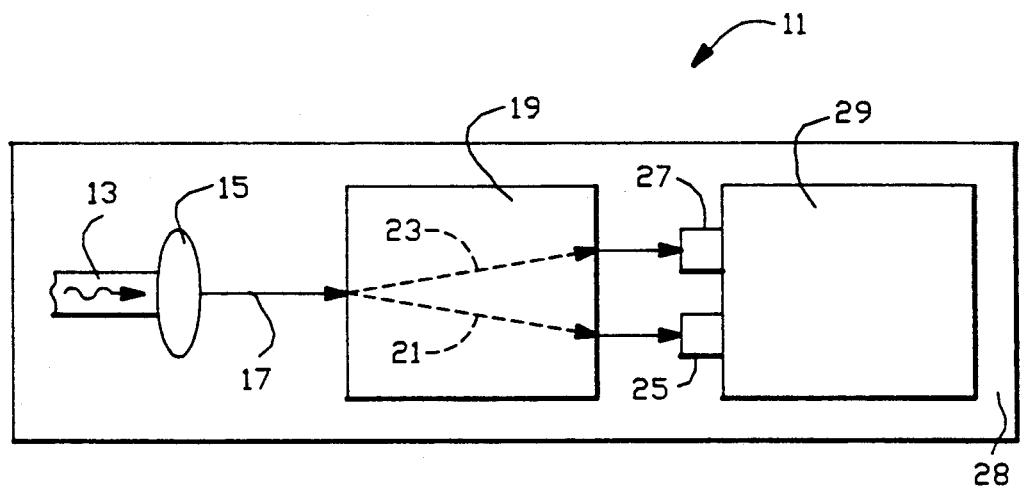
FIG. 1 is a plan view of a first embodiment of the invention that determines a state of linear polarization, including magnitude and angle, of an incident light wave.

With reference to FIG. 1, in a first embodiment 11 of the invention, an optical fiber 13 or other light wave delivery means delivers a light wave to a lens 15 or other optical focusing element that directs the light wave as a ray 17 to a selected position on an adjacent surface of a polarization beam splitter element 19. The optical fiber 13 is preferably a single mode fiber and may be, but need not be, a polarization-maintaining fiber. Optionally, the fiber end may be provided with an anti-reflection coating to increase the magnitude of the light wave signal delivered to the lens 15 and beam splitter element 19. The beam splitter element 19 may, for example, be a birefringent crystal having a different refractive index for each of the two orthogonal polarization components that define the polarization vector associated with the incident light wave. The birefringent crystal may be a uniaxial crystal composed of calcite, rutile or other material that is naturally birefringent; or the crystal may be one that manifests stress-induced birefringence. The lens 15 may have an antireflection coating to increase transmission of the incident light beam or may be a graded index (GRIN) lens that focuses incident light by use of an optically transparent material with variable refractive index.

The two orthogonal polarization components produced by the birefringent crystal travel different paths 21 and 23 within the beam splitter element 19 so that, when the two rays containing these two components reach an opposite surface of the beam splitter element 19, the two rays are separated spatially by a distance of the order of 1 mm or more. In one embodiment using calcite, the angular separation caused by the refractive index difference is about 6°. The two polarization rays that travel the optical paths 21 and 23 are received by two light detectors or other transducers 25 and 27, respectively, and produce two electrical signals representing light intensities that are processed by an electronics module 29. This processing produces a measurement of the length of each of the two orthogonal polarization components $I_x$ and $I_y$ of the original light wave, and from this an equivalent linear polarization vector can be produced, whose length is the square root of the sum of the squares of the lengths of the two components $[I_x^2+I_y^2]^{\frac{1}{2}}$ and whose angle relative to one of the two polarization axes is the arctangent of the ratio of the lengths of the two polarization components $\tan^{-1}[I_y/I_x]$.

A small portion of the light incident on one or both of the transducers 25 and 27 in FIG. 1 may be reflected back toward the beam splitter element 19 if not otherwise controlled. If the normals to the planes of these transducer elements are oriented at non-zero angles relative to the ray direction of the incident light beams, the reflected portions of the light beams incident on the transducers 25 and 27 may be directed in directions away from the beam splitter element 19 and the transducers 25 and 27. The transducer elements themselves may be photodiodes whose light sensitive material is Si, Ge, GaAs, InGaAs or InSb. The diameter of the light sensitive material of the photodiodes should preferably be small so that a pair of the transducers can be positioned on a substrate 28 with a small separation from one another. The substrate 28 may be an electrically insulating material or may be a semiconductor material so that the electronic circuits for signal processing may be set down on the substrate.

However, it may occur that the incident light wave is not polarized linearly but is circularly polarized or, more generally, elliptically polarized. In this instance, a single measurement of the lengths of two polarization components is not sufficient to determine the elliptical polarization state of the incident light wave, and another approach is required.

Figure 2:
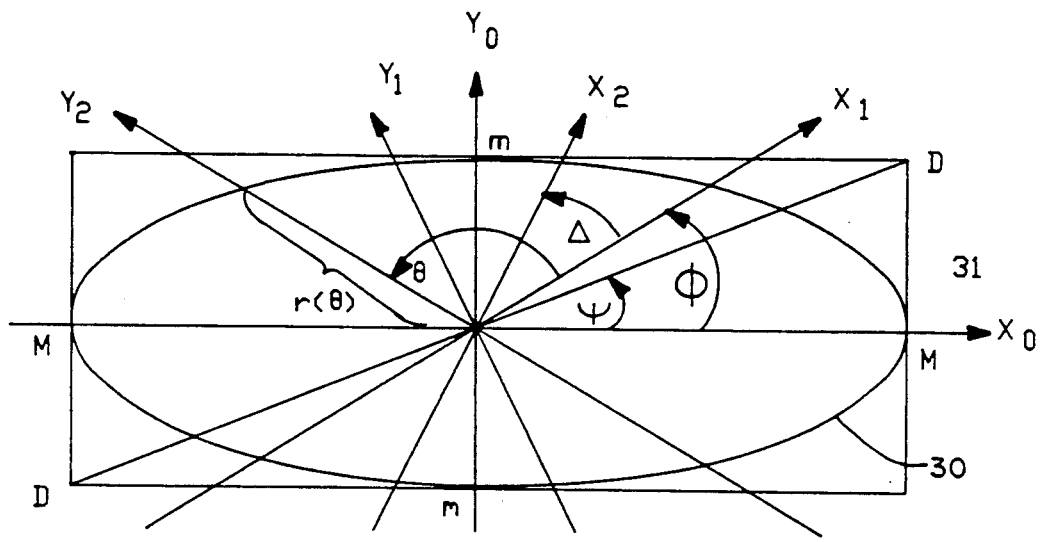
FIG. 2 is a graphic view of the polarization state of an elliptically polarized light beam, when viewed from each of three different two-dimensional Cartesian coordinate systems $(x_0,y_0)$, $(x_1, y_1)$ and $(x_2, y_2)$.

In FIG. 2, an ellipse 30 represents the polarization state of a received electromagnetic signal and having major and minor axes MM and mm, respectively. Referred to its principal axes, the state of polarization is described by the 2×1 Jones vector $$\begin{bmatrix} \cos\Psi \\ -j\sin\Psi \end{bmatrix} (j^2 = -1),$$

where $\Psi$, initially unknown, is the ellipticity angle or angle between the major axis MM of the ellipse 30 and a diagonal DO of a rectangle 31 that inscribes the ellipse. The ellipticity angle $\Psi$ and the ellipticity $\epsilon$ of the ellipse 30 are related by the equation $$\epsilon = 1 - \tan^2\Psi (0 \leq \Psi \leq \pi/4) \qquad (1)$$

The first measurement of the polarization components, made by the two transducers 25 and 27 shown in FIG. 1, defines a new Cartesian coordinate system $(x_1,y_1)$ whose coordinate axes are rotated by an initially unknown angle $\phi$ from the major axis of the rectangle 31. Applying a rotation by the angle $\phi$ to the Jones vector above, the resulting Jones vector becomes $$\begin{bmatrix} \cos\phi\cos\Psi + j\sin\phi\sin\Psi \\ -\sin\phi\cos\Psi + j\cos\phi\cos\Psi \end{bmatrix}.$$

The normalized detected intensities $I_{1x}$ and $I_{1y}$ ($I_{1x}+I_{1y}=1$) on the axes $(x_1,y_1)$ are then the squared moduli of these Jones vector components $$I_{1x} = \cos^2\phi\cos^2\Psi + \sin^2\phi\sin^2\Psi, \qquad (2)$$

$$I_{1y} = \sin^2\phi\cos^2\Psi + \cos^2\phi\sin^2\Psi, \qquad (3)$$

where the usual normalization condition $I_{1x}+I_{1y}=1$ for the intensities is preserved. It is further verified that $$I_{1x} - I_{1y} = \cos 2\phi \cos 2\Psi. \qquad (4)$$

A second polarization measurement is now made, relative to a new Cartesian coordinate system $(x_2,y_2)$ that is rotated from the rectangle major axis by an angle $\phi + \Delta$, where $\Delta$ is a controllable angle ($0 < \Delta < 2\pi$). This yields two new normalized detected intensities $I_{2x}$ and $I_{2y}$ that satisfy $$I_{2x} - I_{2y} = \cos 2(\phi+\Delta)\cos 2\Psi. \qquad (5)$$

Although the angle $\phi$ is unknown, the angle $\Delta$ is known and controllable. It is easily verified that, for the convenient choice $\Delta = \pi/4$ radians the ratio $$(I_{2x} - I_{2y})/(I_{1x} - I_{1y}) = -\tan 2\phi \qquad (6)$$

so that $$\phi = -\tfrac{1}{2}\tan^{-1}[(I_{2x}-I_{2y})/(I_{1x}-I_{1y})] \qquad (7)$$

For a more general choice of the angle $\Delta$ it is easily verified that $$(I_{2x} - I_{2y})/(I_{1x} - I_{1y}) = \cos 2\Delta - \sin 2\Delta \tan 2\phi \qquad (8)$$

so that the unknown angle $\phi$ is determined by $$\phi = \tfrac{1}{2}\tan^{-1}[\cot 2\Delta - \csc 2\Delta (I_{2x}-I_{2y})/(I_{1x}-I_{1y})] \qquad (9)$$

Once the rotation angle $\phi$ is determined the unknown ellipticity angle $\Psi$ is determined from Eq. (4) to be $$\Psi = \tfrac{1}{2}\cos^{-1}[(I_{1x}-I_{1y})\sec 2\phi], \qquad (10)$$

$$\epsilon = 1 - \tan^2\Psi = 2(I_{1x}-I_{1y})\sec 2\phi/[1+(I_{1x}-I_{1y})\sec 2\phi]. \qquad (11)$$

This determines the parameters needed to specify the polarization state of the received signal. If the detected intensities are not normalized so that $I_{1x}+I_{1y} \neq 1$, these intensities may be divided by the sum $I_{1x}+I_{1y}$ to produce the normalized intensities used in the preceding equations. If the measurements produce unnormalized intensities $A_{1x}$ and $A_{1y}$, the normalized intensities would be formed as $I_{1x}=A_{1x}/(A_{1x}+A_{1y})$ and $I_{1y}=A_{1y}/(A_{1x}+A_{1y})$.

Many equivalent methods of determining the ellipse parameters $\phi$, 2a (major axis length) and 2b (minor axis length) may be used. One equivalent method expresses the square of the length of the radius vector or intercept $r(\Theta)$ from the center to the perimeter of the ellipse by $$\frac{1}{r(\Theta)^2} = \frac{\cos^2(\phi+\theta)}{a^2} + \frac{\sin^2(\phi+\theta)}{b^2}, \qquad (12)$$

where a, b and $\phi$ are unknown. For the choices $\Theta=0$, $\pi/2$, $\Delta$ and $\Delta+\pi/2$ ($\Delta$ known and controllable), corresponding to the intercepts of the ellipse in FIG. 2 on the $x_1$, $y_1$, $x_2$ and $y_2$ axes, respectively, the four squares of the lengths $r(\Theta)^2$ are determined by measurement of the light beam polarization intensity components $A_{1x}$, $A_{1y}$, $A_{2x}$, $A_{2y}$ as discussed above and are not normalized quantities. Using Eq. (12) and these four measurements, the following equations are found to determine the unknown values a, b and $\phi$:

$$\tan 2\phi = \cot(2\Delta) -$$

$$\csc(2\Delta)\left(\frac{1}{r(\Delta)^2} - \frac{1}{r(\Delta + \pi/2)^2}\right) / \left(\frac{1}{r(0)^2} - \frac{1}{r(\pi/2)^2}\right) \quad (13)$$

$$1/a^2 = (1+\sec 2\phi)/2r(0)^2 + (1-\sec 2\phi)/2r(\pi/2)_2. \quad (14)$$

$$1/b^2 = (1-\sec 2\phi)/2r(0)^2 + (1+\sec 2\phi)/2r(\pi/2)^2. \quad (15)$$

Description of these two methods of determining the ellipse parameters and orientation should not be taken to exclude other equivalent methods of determining parameters that adequately describe the ellipse.

The determination of the parameters needed to specify the polarization state of the received angle requires the determination of a first set and a second set of polarization components, relative to two sets of Cartesian coordinate axes that are rotated by a controllable angle $\Delta$ relative to one another. These measurements may be performed in the embodiment 32 of the invention shown in FIG. 3. An optical fiber 33 or other light delivery means delivers a light wave to a lens 35 or other optical focusing element that directs the light as a ray 37 to a beam splitter 39. A first portion of the light ray 37 is transmitted as a ray 41 by the beam splitter 39 and is received at a selected position on an adjacent surface of a first polarization beam splitter element 49. The beam splitter element 49 may be a birefringent crystal as in FIG. 1, and produces two orthogonal polarization components that travel through the beam splitter element 49 by two diverging paths 51 and 53. These first two polarization components are received by two optical detectors or other transducers 55 and 57 and produce two electrical signals, analogous to $I_{1x}$ and $I_{1y}$ or to the unnormalized intensities $A_{1x}$ and $A_{1y}$ above, that are processed by an electronics module 69.

A second component of the light ray 37 is reflected by the beam splitter 39 and proceeds as a second ray 43 to a fully reflecting mirror 45 that directs a twice-reflected ray 47 to a selected position on an adjacent surface of a second polarization beam splitter element 59. The second beam splitter element 59 may also be a birefringent crystal, with transverse crystal axes rotated by an angle $\Delta$ relative to the transverse crystal axes of the first beam splitter element 49, that splits the ray 47 into two orthogonal polarization components that travel along diverging optical paths 61 and 63 within the beam splitter element 59. A convenient choice of $\Delta$ is $\Delta = 45°$. These third and fourth polarization components are received by two optical detectors 65 and 67 and produce two electrical signals, analogous to the signals $A_{2x}$ and $A_{2y}$, respectively, discussed above. These third and fourth electrical signals are also processed by the electronics module 69. The processing of the four electrical signals produced at the optical detectors 55, 57, 65 and 67, in one embodiment, uses the analysis set forth in Eqs. (1)–(11) or Eqs. (12)–(15) to determine the polarization state of the signal received on the optical fiber 33. A substrate 71, similar to the substrate 28 shown in FIG. 1, may be provided to hold or act as support for the other items shown in FIG. 3.

Figure 4:
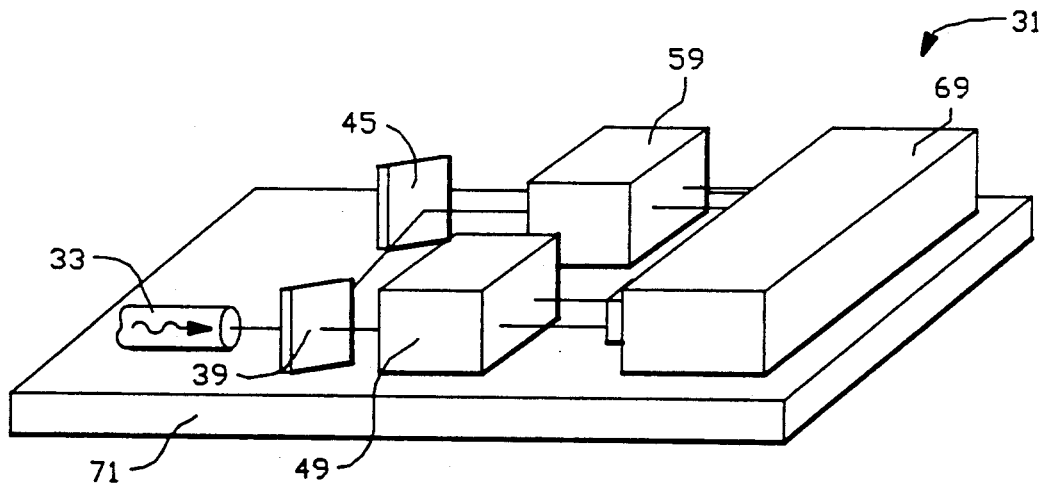
FIG. 4 is a perspective view of a chip containing the embodiment of the invention illustrated in FIG. 3.

FIG. 4 illustrates how the system 32, or the system 11 in a simpler embodiment, may be assembled on a single chip. In this instance, the dimension of the substrate 71 may be less than 4 cm and the two polarization beam splitter elements 49 and 59 may have linear dimensions no more than a few cm.

Figure 5:
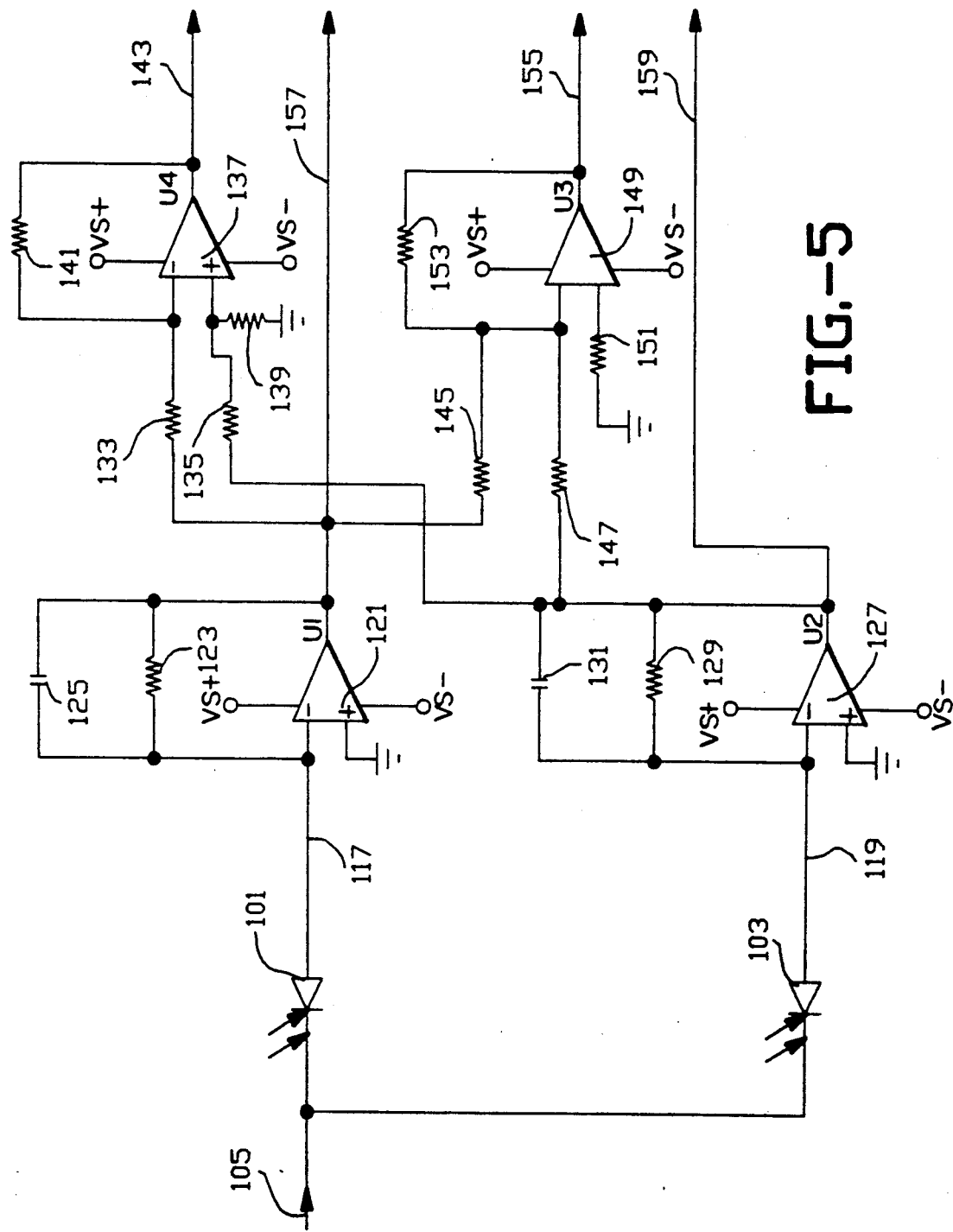
FIG. 5 is an electrical schematic plan of a circuit that produces the sum and difference of two photodetector signals.

FIG. 5 is an electronics schematic diagram illustrating one means of forming some of the electrical signals needed to determine the complete polarization state of a signal that arrives on an optical fiber 13 in FIG. 1. Two orthogonal polarization beam components are received by the respective photodiodes 101 and 103. The cathode of each of the photodiodes 101 and 103 is biased by a positive voltage source 105 as shown. The electrical signals produced at the photodiodes 101 and 103 then travel along the respective signal paths 117 and 119, where these two signals are received at the negative input terminals of two operational amplifiers 121 and 127, respectively. The positive input terminal of the amplifier 121 is grounded, and the negative input terminal thereof is connected by a resistor 123 and a capacitor 125, connected in parallel, to the output terminal of the amplifier 121. Similarly, the positive input terminal of the amplifier 127 is grounded, and the negative input terminal thereof is connected through a resistor 129 and a capacitor 131, arranged in parallel, to the output terminal of the amplifier 127. The amplifiers 121 and 127 issued amplifications of the output signals received at the photodiodes 101 and 103, respectively.

The remainder of the circuit shown in FIG. 5 is optional and may be included in the substrate 71 shown in FIG. 4 or may be implemented using signal processing apparatus, such as a microprocessor, that is not positioned in the chip. The output signals from the amplifiers 121 and 127 are passed through two resistors 133 and 135, respectively, to the negative and positive input terminals of a third operational amplifier 137. The positive input terminal of the amplifier 137 is grounded through a resistor 139, and the negative input terminal is connected through a resistor 141 to the output terminal of the amplifier 137. The output signal from the amplifier 137 is the difference of the two electrical signals, suitably amplified, produced at the photodiodes 101 and 103.

The output signals from the amplifiers 121 and 127 are passed through two resistors 145 and 147, respectively, to the negative input terminal of a fourth operational amplifier 149. The positive input terminal of the amplifier 149 is grounded through a resistor 151, and the negative input terminal thereof is connected through a resistor 153 to the output terminal of the amplifier 149. The output signal from the amplifier 149 is the negative sum of the two electrical signals, suitably amplified, that are produced at the photodiodes 101 and 103, and this sum appears on a signal output line 155.

Figure 6:
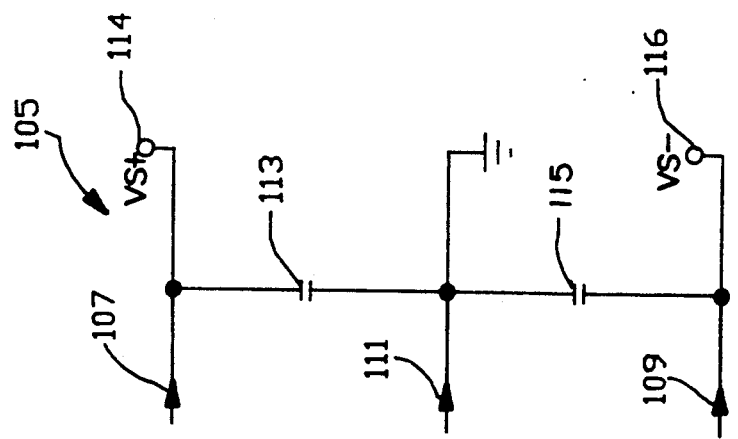
FIG. 6 is an electrical schematic detail of a circuit for the voltage source used in FIG. 5.

FIG. 6 illustrates one embodiment for the positive voltage source 105, which consists of a positive voltage source 107, a negative voltage source 109 having equal voltage magnitude, a source 111 of ground voltage potential, with the output terminal of the positive voltage source 107 and the ground voltage source 111 being connected by a capacitor 113, and with the output terminals of the negative voltage source 109 and the ground voltage source 111 being connected through a capacitor 115. The desired positive or negative voltages then appear at the respective voltage source output terminals 114 and 116, respectively.

Figure 3:
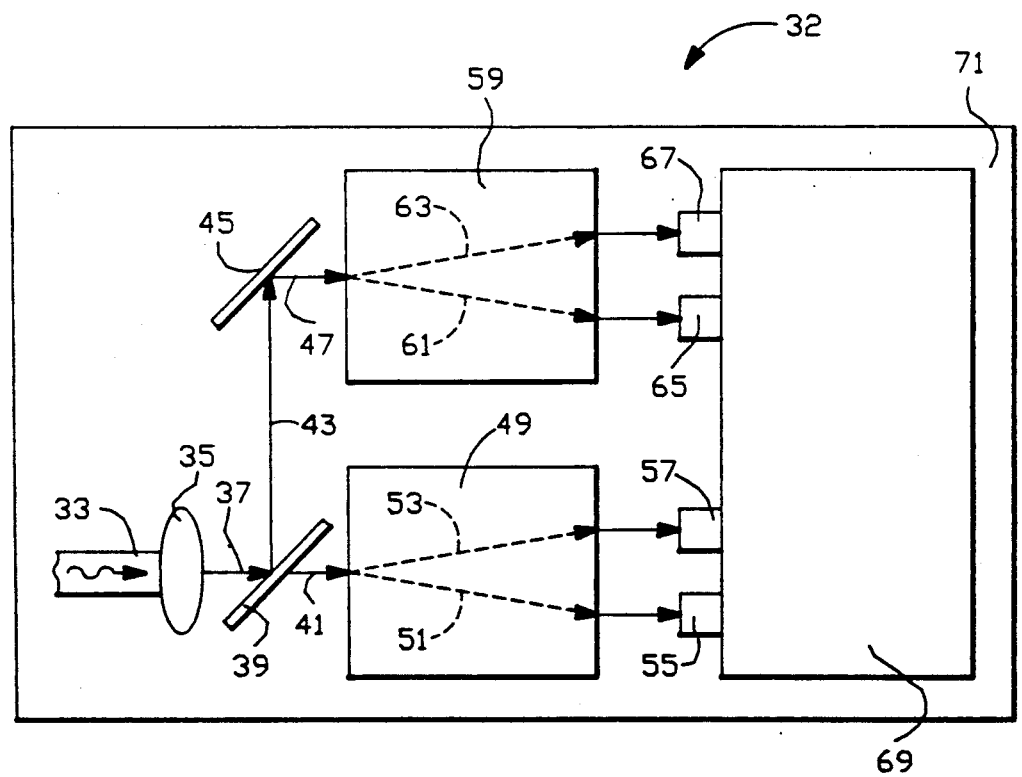
FIG. 3 is a plan view of a second embodiment of the invention, in which the state of elliptical polarization of an incident light wave can be determined, with the exception of the direction of rotation.
Figure 7:
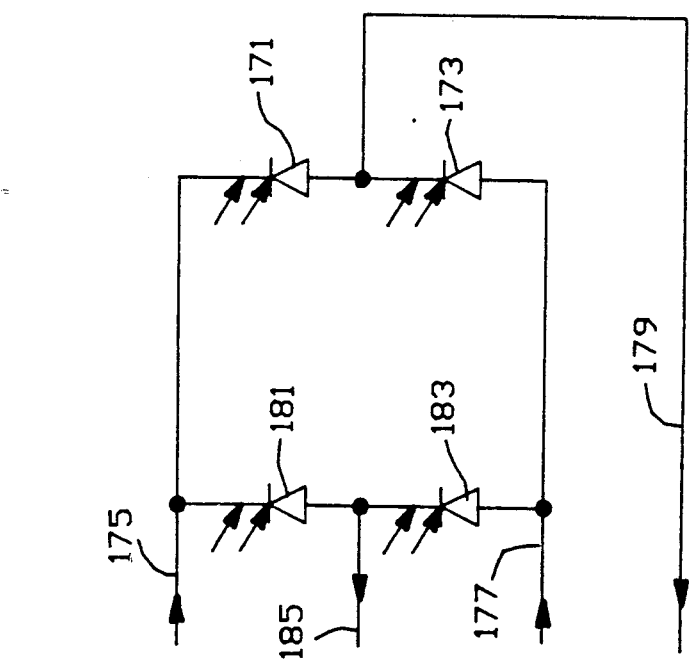
FIG. 7 is an electrical schematic detail of a photodetector circuit suitable for reducing the dark current that is otherwise present at the photodetectors shown in FIG. 5.

FIG. 7 illustrates an alternative arrangement of four photodetectors for converting the polarization components received at the transducers shown in FIGS. 1 and 3 to electrical signals. This arrangement is useful in reducing the dark current that is present in unusual environments such as a high temperature environment. The anode of a first photodetector 171 is connected to the cathode of a second photodetector 173, with the cathode of the first photodetector being connected to a positive voltage source 175 and the anode of the second photodetector being connected to a negative voltage source 177. The photodetector 171 is exposed to the optical signal representing one of the polarization beam components, and the second photodetector 173 is covered so that it receives no optical stimulation. The anode of the first photodetector 171 is connected to a first output signal line 179. In a similar manner, the anode of a third photodetector 181 is connected to the cathode of a fourth photodetector 183, with the cathode of the third photodetector being connected to the positive voltage source 175 and the anode of the fourth photodetector being connected to the negative voltage source 177. The third photodetector is exposed to optical stimulation, and the fourth photodetector is covered and receives no optical stimulation. The anode of the third photodetector 181 is connected to a second output signal line 185.

If the double beam splitter embodiment shown in FIG. 3 is used here, a second circuit that is substantially identical to the circuit shown in FIG. 5 is provided to produce and amplify the transducer electrical signals and to produce the sum and difference signals for the second pair of beam polarization components. To determine the total polarization state, Eqs. (7) and (10) (for $\Delta = \pi/4$), or alternatively Eqs. (9) and (10) (for a general rotation angle $\Delta$) are formed from the signal differences that appear on the output line 143 in FIG. 5 and on the analogous output signal line for the circuit that is identical to the circuit shown in FIG. 5.

Figure 8:
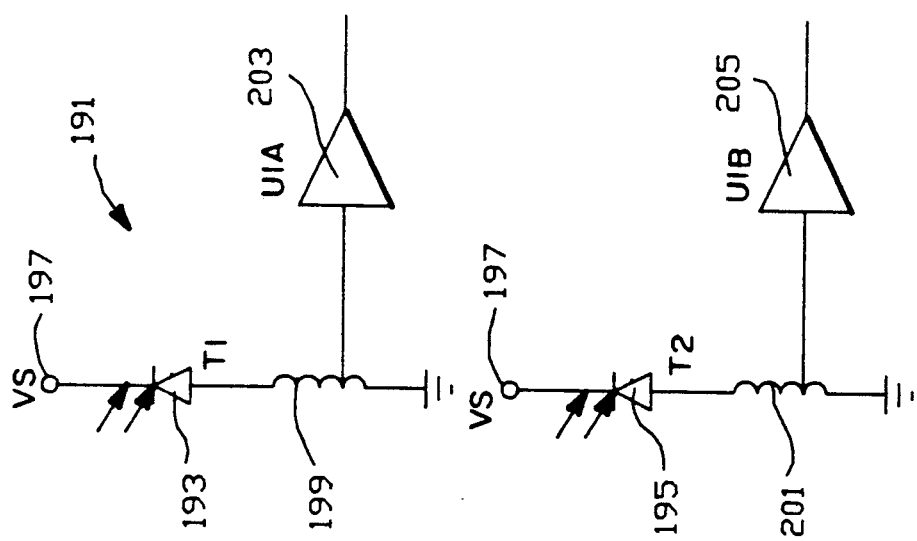
FIG. 8 is an electrical schematic detail of a circuit that provides wide band amplification for the photodetector signals in the invention.

FIG. 8 illustrates an embodiment of the electronics that can replace the more complex embodiment shown in FIG. 5. Two orthogonal polarization beam components are received by the respective photodiodes 193 and 195. The cathode of each photodiode 193 and 195 is biased by a positive voltage source 197. The anodes of the two photodiodes 193 and 195 are connected to the upper voltage terminals of two high frequency transformers 199 and 201, respectively. Taps on the transformers 199 and 201 are connected to wide band amplifiers 203 and 205, respectively, with respective output terminals that issue amplifications of output signals that were generated at the respective photodiodes 193 and 195.

The two transformers 199 and 201 each have a 1:4 turns ratio and serve to connect the photodiode signals to a 50-Ohm or 75-Ohm impedance at the input terminals of the amplifiers 203 and 205. Use of the transformers 199 and 201 in the signal path allows amplification of signals with frequencies in the range 5–600 MHz, or even higher, with minimum noise, and allows use of signals with about twice the power vis-a-vis the maximum available without the use of such transformers).

In another embodiment of this invention the Polarization Diversity Receiver (PDR) is used to detect two separate communication channels which are launched in a single mode fiber with orthogonal polarizations. A polarization controller, positioned in front of the PDR, adjusts the state of polarization of the incoming light so that each information channel falls on a separate detector. This controller can be eliminated when a polarization-maintaining fiber aligned with the PDR axis is used. This technique is useful in fiber optic transmission of Amplitude Modulation Vestigial Side Band signals. In this application, signals in the frequency regime 50–300 MHz are transmitted with one linear polarization and received by a first photodetector 193 and signals in the 300–600 MHz range are transmitted with orthogonal linear polarization and are detected by a second photodetector 195 in FIG. 8. After the two signals are filtered, the output signals of the two amplifiers are summed on a single coaxial cable and are transmitted to the customer premises. To eliminate the need for a polarization controller, a polarization-maintaining fiber may be used where the 50–300 MHz signals are aligned on one axis and the 300–600 MHz signals aligned on the other axis of the fiber. Correspondingly, the PDR detectors 193 and 195 are aligned with the fiber axis and orthogonal to one another. One advantage of this embodiment is the reduced bandwidth demand from each photodetector amplifier. Since the light is separated into two non-overlapping frequency bands, the RF harmonics from one of the bands are precluded from interfering with signals that appear in the other of the bands. The above described example can be applied to digital communication as well.

The determination of the full elliptical polarization state (with the exception of direction of rotation) by use of the apparatus in FIG. 3 is performed in real time but requires the use of two polarization beam splitter elements 49 and 59, and four transducers 55, 57, 65 and 67. The full elliptical polarization state (again, with the exception of direction of rotation) can also be determined by use of the embodiment 211 shown in FIG. 9. An optical fiber 213 or other optical transmission means transports a light wave with polarization to a lens 215 or other optical focusing element that focuses and directs the light wave 217 to a selected position on an adjacent surface of a polarization beam splitter element 219. The beam splitter element 219 splits the beam into two orthogonal polarization components that define the light wave polarization vector, and light rays 221 and 223 with the two polarization components propagate to and are received by two transducers 225 and 227. Thus far, the operation is analogous to the operation of the apparatus shown in FIG. 1.

A rotating wave plate 231 is positioned between the optical fiber 213 and the polarization beam splitter 219 to modulate or vary the direction of the instantaneous polarization vector that is sensed and split by the beam splitter 219. The lens 215 may be positioned between the fiber 213 and the rotating wave plate 231 or between the plate 231 and the beam splitter 219. If the instantaneous light wave polarization vector is assumed frozen at a time $t = t_f$ and has the two-dimensional polarization intensity components $(A_f \cos\Theta_f, A_f \sin\Theta_f)$ at that time, a wave plate having constant associated angular velocity $\omega$ will produce a light wave polarization vector at time $t > t_f$ having the intensity components $(A_f \cos[\Theta - \omega(t - t_f)], A_f \sin[\Theta - \omega(t - t_f)])$. The effect of the wave plate modulation is to rotate the instantaneous (frozen) polarization vector by an angular amount depending on a time difference $t - t_f$, or, equivalently to rotate the initial two-dimensional Cartesian coordinate system $(x_1, y_1)$ by the negative of this angular amount to produce a new Cartesian coordinate system $(x_2, y_2)$, as illustrated in FIG. 2.

Assume that the light wave polarization vector issued from the end of the optical fiber 213 is the same (unchanged) at and between two times $t=t_1$ and $t=t_2>t_1$. The polarization vector, as received at the two transducers 225 and 227, at the time $t_2$ will differ from the polarization vector at the time $t_1$ by an angle of rotation $\Delta$ given by $$\Delta = \omega(t_2 - t_1). \tag{11}$$

Measurement of the two polarization components received at the two transducers 225 and 227 at the times $t=t_1$ and $t=t_2$ will produce the four components needed for the analysis discussed in connection with Eqs. (1)–(11) or (12)–(15) above so that a determination of the full polarization state, with the exception of direction of rotation, can be made.

In order to perform the measurement of the light wave polarization vector components for the two times $t_1$ and $t_2$, a clock 233 is provided that delivers a sequence of periodic clock pulses to a measurement and storage module 229 that receives the electrical signals from the transducers 225 and 227. As the measurement module 229 receives each clock pulse, the module records and stores the instantaneous values of the two polarization components received at the two transducers 225 and 227. If the clock pulse period is $T = \Delta/\omega$, the two measurements made at a given clock pulse plus the two measurements made at the next consecutive clock pulse will provide the four components $I_{1x}$, $I_{1y}$, $I_{2x}$ and $I_{2y}$ (or $A_{1x}$, $A_{1y}$, $A_{2x}$ and $A_{2y}$) needed for determination of the full polarization state according to Eqs. (1)–(11) or (12)–(15) above. The measurements $I_{1x}$ and $I_{1y}$ will be made at a different time than the measurements of $I_{2x}$ and $I_{2y}$ so that the total measurement is not made in real time. However, the simpler system shown in FIG. 9 may be used rather than the more complex system shown in FIG. 3. The time difference $T=t_2-t_1$ at which the two sets of measurements are made is limited primarily by the ability of the module 229 to reactivate itself for the next consecutive measurement.

Figure 9:
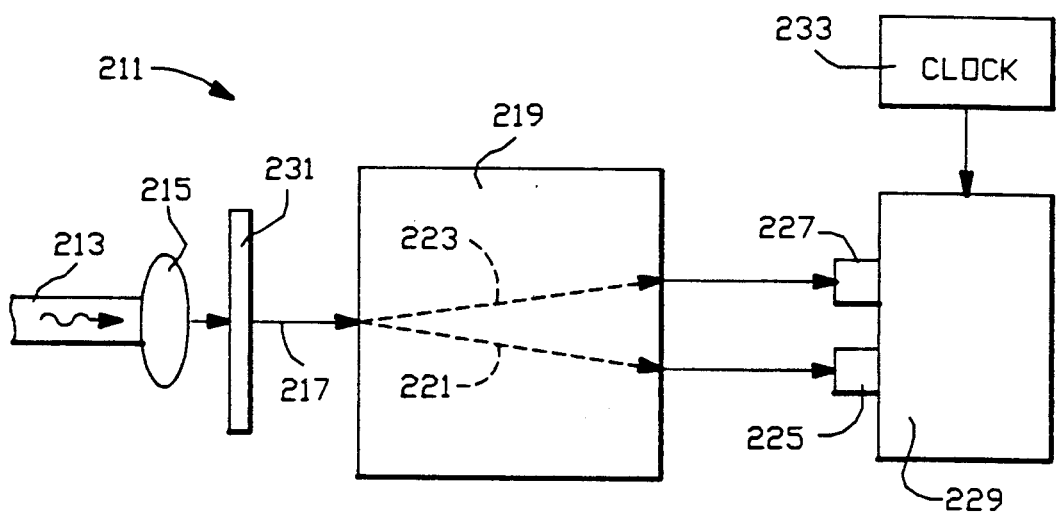
FIG. 9 is a plan view of a third embodiment of the invention, in which the state of elliptical polarization of an incident light wave is determined, with the exception of direction of rotation.

The embodiments shown in FIGS. 3 and 9 may be used to implement digital communications using two or more communication channels along the axis of a polarization maintaining fiber ("PMF"). Two orthogonal polarization channels can be employed on the fiber, with the information transmitted being switched between the two channels in a manner analogous to the use of two distinct symbols in Morse code telegraphy. More than two channels may be provided for information transmission on the fiber, limited only by the need to accurately distinguish between the channels. If the same information is switched between two such channels, the PDR can work as a push-pull receiver-amplifier. One advantage of this configuration is increase by a factor of two in the amount of energy per unit time transmitted by the fiber.

In analog communication applications, such as CATV, of the PDR, each of two orthogonal axes of a PMF may be used to transmit information on a different group of channels. Each receiver operates over a limited spectral bandwidth, and the amount of optical power transmitted on each channel can be increased without saturating the amplifier. For example, in FIG. 3 a first beam splitter 49 and associated detector might have a receiving band of 5–300 MHz, and a second beam splitter 59 and associated detector might have a receiving band of 301–600 MHz. Each detector could be isolated from harmonics generated by channels using the other detector and orthogonal polarization.

Figure 10:
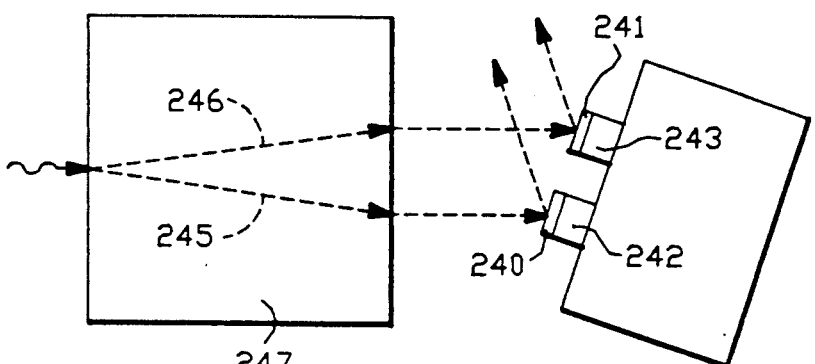
FIGS. 10 and 11 are plan views of further embodiments of the invention with alternate optical configurations.

The transducer pairs in FIGS. 1, 3 and 9 are preferably positioned so that none of the light received from the corresponding polarization beam splitter is reflected back to the beam splitter component. Several methods of accomplishing this are available. In FIG. 10, two photosensitive windows 240 and 241 of two transducers 242 and 243, respectively, are each oriented to receive two light beams 245 and 246, respectively, from a polarization beam splitter 247 at non-zero incidence angles so that any specular reflection from the windows 240 and 241 is not directed back toward the beam splitter 247 or the beam delivery means.

Figure 12:
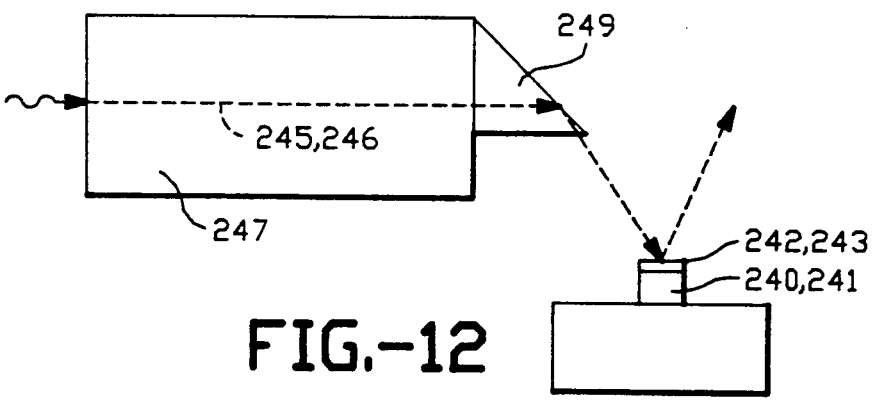
FIG. 12 is a side view of the embodiment of FIG. 11.
Figure 11:
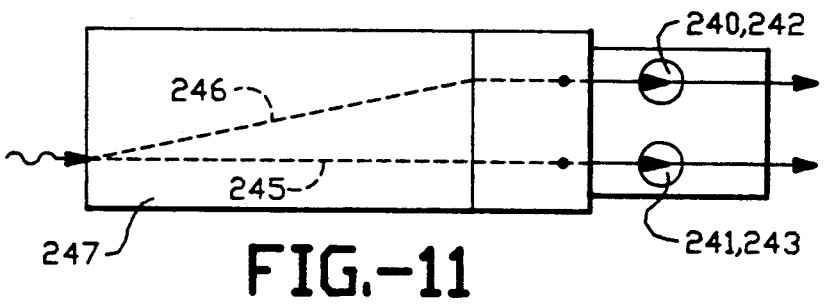

In the plan view in FIG. 11, a prism 249 is positioned to receive the light beams 245 and 246 from the polarization beam splitter 247 and to reflect this light by total internal reflection toward the radiation-receiving windows 240 and 241, respectively, of the transducers 242 and 243, respectively, at non-zero incidence angles. A portion of the light received at the windows 240 and 241 is specularly reflected therefrom in a direction that does not strike the beam splitter, the beam delivery means or the other transducer. FIG. 12 is a side view of the embodiment shown in FIG. 11, illustrating the direction of specular reflection of a portion of the incident light beams at the windows 240 and 241.

We claim:

1. Apparatus for detection of the linear polarization vector of a light beam, the apparatus comprising:

a substrate;

a polarization beam splitter, positioned on the substrate to receive an incident light beam, to produce a first light beam that is linearly polarized in a first direction, to produce a second light beam that is linearly polarized in a second, perpendicular direction, and to cause the first and second light beams to travel along different optical paths within the beam splitter and to issue at different positions from the beam splitter;

beam direction means positioned on the substrate, for receiving an incident light beam and for directing the light beam toward a selected position at the beam splitter;

a first transducer, positioned on the substrate to receive the first light beam from the beam splitter, to convert the first light beam energy to a first electrical signal, and to issue this signal at an output terminal;

a second transducer, positioned on the substrate to receive the second light beam from the beam splitter, to convert the second light beam energy to a second electrical signal, and to issue this signal at an output terminal;

circuit means for receiving and amplifying the first and second electrical signals, wherein said circuit means includes:

a first transformer having one voltage terminal that is held at a fixed reference voltage, having a second voltage terminal that is connected to said output terminal of said first transducer, and having a transformer tap to issue a transformer output signal;

a second transformer having one voltage terminal that is held at a fixed reference voltage, having a second voltage terminal that is connected to said output terminal of said second transducer, and having a transformer tap to issue a transformer output signal;

a first amplifier having an input terminal connected to the first transformer tap and having an output terminal, to receive and amplify an input signal; and a second amplifier having an input terminal connected to the second transformer tap and having an output terminal, to receive and amplify an input signal.

2. Apparatus for determination of the polarization state in a light beam, the apparatus comprising:

a substrate;

a first polarization beam splitter, positioned on the substrate to receive an incident light beam, to produce a first light beam that is linearly polarized in a first direction, to produce a second light beam that is polarized in a second, perpendicular direction, and to cause the first and second light beams to travel along different optical paths within the first beam splitter and to issue at different positions therefrom;

a second polarization beam splitter, positioned on the substrate to receive an incident light beam, to produce a third light beam that is linearly polarized in a third direction, to produce a fourth light beam that is linearly polarized in a fourth direction perpendicular to the third direction, and to cause the third and fourth light beams to travel along different optical paths within the second beam splitter and to issue at different positions therefrom, where the first and third light beam polarization directions are rotated by a selected non-zero angle $\Delta$ relative to one another;

beam splitter means positioned on the substrate, for receiving a light beam, for directing a first portion of the light beam toward a selected position at the first polarization beam splitter, and for directing a second portion of the light beam toward a selected position at the second polarization beam splitter;

first, second, third and fourth transducers, positioned on the substrate to receive the first light beam, second light beam, third light beam and fourth light beam, respectively, from the first and second polarization beam splitters and to convert the energy in the light beams into first, second, third and fourth electrical signals $A_{1x}$, $A_{1y}$, $A_{2x}$ and $A_{2y}$, respectively; and circuit means for receiving and amplifying the first, second, third and fourth electrical signals, wherein said circuit means includes means for forming a first ratio $R_1 = (A_{1x} - A_{1y})/(A_{1x} + A_{1y})$, for forming a second ratio $R_2 = (A_{2x} - A_{2y})/(A_{2x} + A_{2y})$, for forming and issuing the quantity $\phi = (\frac{1}{2}) \tan^{-1}[\cot(2\Delta) - \csc(2\Delta) R_2/R_1]$ as the angle between said first coordinate axis and the major axis of said polarization ellipse, and for forming the quantity $\epsilon = 2R_1 \sec 2\phi/[1 + R_1 \sec 2\phi]$ as the ellipticity of said polarization ellipse.

3. Apparatus for determination of the polarization state in a light beam, the apparatus comprising:

a substrate;

a first polarization beam splitter, positioned on the substrate to receive an incident light beam, to produce a first light beam that is linearly polarized in a first direction, to produce a second light beam that is polarized in a second, perpendicular direction, and to cause the first and second light beams to travel along different optical paths within the first beam splitter and to issue at different positions therefrom;

a second polarization beam splitter, positioned on the substrate to receive an incident light beam, to produce a third light beam that is linearly polarized in a third direction, to produce a fourth light beam that is linearly polarized in a fourth direction perpendicular to the third direction, and to cause the third and fourth light beams to travel along different optical paths within the second beam splitter and to issue at different positions therefrom, where the first and third light beam polarization directions are rotated by a selected non-zero angle relative to one another;

beam splitter means positioned on the substrate, for receiving a light beam, for directing a first portion of the light beam toward a selected position at the first polarization beam splitter, and for directing a second portion of the light beam toward a selected position at the second polarization beam splitter;

first, second, third and fourth transducers, positioned on the substrate to receive the first light beam, second light beam, third light beam and fourth light beam, respectively, from the first and second polarization beam splitters and to convert the energy in the light beams into first, second, third and fourth electrical signals $A_{1x}$, $A_{1y}$, $A_{2x}$ and $A_{2y}$, respectively; and circuit means for receiving and amplifying the first, second, third and fourth electrical signals wherein said circuit includes means for forming a ratio $$R = [(A_{2x})^{-1} - (A_{2y})^{-1}]/[(A_{1x})^{-1} - (A_{1y})^{-1}],$$

for forming and issuing the quantity $$\phi = (\tfrac{1}{2}) \tan^{-1}[\cot(2\Delta) - \csc(2\Delta) R]$$

as the angle between said first coordinate axis and said major axis of said polarization ellipse, and for forming and issuing the quantities $$a = [(1 + \sec 2\phi)(A_{1x})^{-1} + (1 - \sec 2\phi)(A_{1y})^{-1}]^{-\frac{1}{2}}$$

$$b = [(1 - \sec 2\phi)(A_{1x})^{-1} + (1 + \sec 2\phi)(A_{1y})^{-1}]^{-\frac{1}{2}}$$

as the lengths of said major and minor axes of said polarization ellipse.

4. Apparatus for detection of the polarization state of a light beam, the apparatus comprising:

a substrate;

a polarization beam splitter, positioned on the substrate to receive an incident light beam, to produce a first light beam that is linearly polarized in a first direction, to produce a second light beam that is linear-ly polarized in a second, perpendicular direction, and to cause the first and second light beams to travel different optical paths within the beam splitter and to issue at different positions from the beam splitter;

beam direction and rotation means positioned on the substrate, for receiving an incident light beam having an associated polarization vector lying in a polarization plane and for directing the light beam toward a selected position at the beam splitter, with the light wave polarization vector being rotated in the plane at constant angular velocity $\omega$ as a function of time;

a clock source to produce and issue a sequence of at least two periodic clock pulses of predetermined period T with associated frequency $f=1/T=\omega/\Delta$, where $\Delta$ is a predetermined angle;

a first transducer, positioned on the substrate to receive the clock pulse sequence from the clock, to receive the first light beam from the beam splitter, and to convert the instantaneous first light beam energy to an instantaneous first amplitude electrical signal $A_{1x}$ as a first clock pulse is received by the first, transducer and to receive a subsequent first light beam from the beam splitter and to convert the subsequent first light beam energy to an instantaneous subsequent first amplitude electrical signal $A_{2x}$ as a next consecutive clock pulse is received by the first transducer;

a second transducer, positioned on the substrate to receive the clock pulse sequence from the clock, to receive the second light beam from the beam splitter and to convert the instantaneous second light beam energy to an instantaneous second amplitude electrical signal $A_{1y}$ as a first clock pulse is received by the second transducer, and to receive a subsequent second light beam from the beam splitter and to convert the subsequent second light beam energy to an instantaneous subsequent second amplitude electrical signal $A_{2y}$ as a next consecutive clock pulse is received by the second transducer;

signal storage means for receiving the first and second amplitude electrical signals from the first and second transducers, for storing these signals for a time interval T, for receiving the subsequent first and subsequent second amplitude electrical signals from the first and second transducers, and for issuing these four signals as first, second, third and fourth electrical signals; and circuit means for receiving and amplifying the first and second electrical signals.

5. The apparatus of claim 4, wherein said circuit means includes means for receiving the first and second electrical signals and the subsequent first and subsequent second electrical signals $A_{1x}$, $A_{1y}$, $A_{2x}$ and $A_{2y}$, respectively, and for determining the lengths of the major axis and minor axis of the ellipse that describes the polarization state of the light beam and for determining the angular orientation of the two ellipse axes relative to first and second coordinate axes defined by the first direction and the second direction at the polarization beam splitter.

6. The apparatus of claim 4, wherein each of said polarization beam splitters is a birefringent crystal, oriented so that a face of the crystal that receives said light beam from said beam direction means lies in a plane of the crystal that has two perpendicular directions therein, with each of these two perpendicular directions having a different refractive index associated therewith.

7. The apparatus of claim 6, wherein each of said birefringent crystals is a uniaxial crystal and is composed of material drawn from the class consisting of calcite and rutile.

8. The apparatus of claim 6, wherein said circuit means includes means for forming a first ratio $R_1=(A_{1x}-A_{1y})/(A_{1x}+A_{1y})$, for forming a second ratio $R_2=(A_{2x}-A_{2y})/A_{2x}+A_{2y})$, for forming and issuing the quantity $\phi=(\frac{1}{2})\tan^{-1}[\cot(2\Delta)-\csc(2\Delta)R_2/R_1]$ as the angle between said first coordinate axis and the major axis of said polarization ellipse, and for forming the quantity $\epsilon=2R_1\sec2\phi/[1+R_1\sec2\phi]$ as the ellipticity of said polarization ellipse.

9. The apparatus of claim 6, wherein said circuit includes means for forming a ratio $R=[(A_{2x})^{-1}-(A_{2y})^{-1}]/[(A_{1x})^{-1}-(A_{1y})^{-1}]$, for forming and issuing the quantity $$\phi=(\tfrac{1}{2})\tan^{-1}[\cot(2\Delta)-\csc(2\Delta)R]$$

as the angle between said first coordinate axis and said major axis of said polarization ellipse, and for forming and issuing the quantities $$a=[(1+\sec2\phi)(A_{1x})^{-1}+(1-\sec2\phi)(A_{1y})^{-1}]^{-\frac{1}{2}}$$

$$b=[(1-\sec2\phi)(A_{1x})^{-1}+(1+\sec2\phi)(A_{1y})^{-1}]^{-\frac{1}{2}}$$

as the lengths of said major and minor axes of said polarization ellipse.

10. The apparatus of claim 4, wherein said transducers are each oriented so that any light that is specularly reflected from a transducer is not directed toward any other transducer or toward either of said polarization beam splitter.

11. The apparatus of claim 4, wherein said light beam is received by said beam direction means from an optical fiber.

12. The apparatus of claim 4, wherein said first and second transducers are photodiodes whose light-sensitive material is drawn from a class consisting of InGaAs, Si, Ge, GaAs, and InSb.

13. The apparatus of claim 12, wherein said light sensitive material of said photodiodes has a diameter of no more than 3 mm.

14. The apparatus of claim 4, wherein said substrate has a diameter of no more than a few cm.

15. A method for detection of the polarization state of a light beam, the method comprising the steps of:

providing a polarization beam splitter to receive an incident light beam, to produce a first light beam that is linearly polarized in a first direction, to produce a second light beam that is linearly polarized in a second, perpendicular direction, and to cause the first and second light beams to travel different optical paths within the beam splitter and to issue at different positions from the beam splitter;

providing beam direction and rotation means positioned on the substrate, for receiving an incident light beam having an associated polarization vector lying in a polarization plane and for directing the light beam toward a selected position at the beam splitter, with the light wave polarization vector being rotated in the plane at constant angular velocity $\omega$ as a function of time;

providing a first transducer to receive the first light beam from the beam splitter and to convert the instantaneous first light beam energy to an instantaneous first electrical signal at a sequence of times $t=t_1, t_2, t_3, \ldots$ drawn from an increasing sequence of times $\{t_n\}_{n=1}^N$, where $t_{2i}-t_{2i-1}=T=\Delta/\omega$, where $\Delta$ is a selected angle ($0<\Delta<2\pi$);

providing a second transducer to receive the second light beam from the beam splitter and to convert the instantaneous second light beam energy to an instantaneous second electrical signal at approximately the sequence of times $t=t_1, t_2, t_3, \ldots$;

providing signal storage means for receiving the first and second electrical signals from the first and second transducers, for storing these signals for a time interval T, and for issuing these signals as first and second stored electrical signals;

circuit means for receiving the first and second electrical amplitude signals and the first and second stored electrical signals, for determining the lengths of the major axis and minor axis of the ellipse that describes the polarization state of the light beam, and for determining the angular orientation of the two ellipse axes relative to first and second coordinate axes defined by the first direction and the second direction at the polarization beam splitter.

* * * * *

UNITED STATES PATENT AND TRADEMARK OFFICE
CERTIFICATE OF CORRECTION

PATENT NO. : 5,102,222
DATED : April 7, 1992
INVENTOR(S) : Josef Berger et al.

It is certified that error appears in the above-identified patent and that said Letters Patent is hereby corrected as shown below:

Column 7, line 15 "$1/a^2=(1+sec2\phi)/2r(0)^2+(1-sec2\phi)/2r(\pi/2)_2$"
should read -- $1/a^2=(1+sec2\phi)/2r(0)^2+(1-sec2\phi)/2r(\pi/2)^2$ --.

Claim 4, column 14, line 56, "linear-ly" should read
-- linearly --.

Claim 15, column 16, line 59, "$\{t_n\}_{n=1}^N$" should read
-- $\{t_n\}_{n=1}^N$ --.

Signed and Sealed this

Tenth Day of August, 1993

Attest:

MICHAEL K. KIRK

*Attesting Officer*  *Acting Commissioner of Patents and Trademarks*